(12) United States Patent
Chen et al.

(10) Patent No.: US 10,271,732 B2
(45) Date of Patent: Apr. 30, 2019

(54) COLOR MEASUREMENT JIG

(71) Applicant: COLGATE-PALMOLIVE COMPANY, New York, NY (US)

(72) Inventors: Xiang Chen, Somerset, NJ (US); Donghui Wu, Bridgewater, NJ (US)

(73) Assignee: Colgate-Palmolive Company, New York, NY (US)

( * ) Notice: Subject to any disclaimer, the term of this patent is extended or adjusted under 35 U.S.C. 154(b) by 504 days.

(21) Appl. No.: 14/968,541

(22) Filed: Dec. 14, 2015

(65) Prior Publication Data
US 2017/0171438 A1 Jun. 15, 2017

(51) Int. Cl.
| A61B 5/00 | (2006.01) |
| H04N 5/225 | (2006.01) |
| A61B 1/24 | (2006.01) |
| A61B 1/05 | (2006.01) |
| A61B 5/103 | (2006.01) |

(52) U.S. Cl.
CPC ............ *A61B 5/0088* (2013.01); *A61B 1/053* (2013.01); *A61B 1/24* (2013.01); *A61B 5/1032* (2013.01); *H04N 5/2251* (2013.01); *H04N 5/2256* (2013.01)

(58) Field of Classification Search
CPC ...... H04N 5/2253; H04N 5/2254; A61B 1/24; A61B 5/0088
USPC ........................................................ 348/66
See application file for complete search history.

(56) References Cited

U.S. PATENT DOCUMENTS

| 3,759,153 | A | | 9/1973 | Aimo et al. |
| 3,969,720 | A | | 7/1976 | Nishino |
| 5,285,228 | A | * | 2/1994 | VanDeMoere ......... G03B 17/02 396/6 |
| 7,711,252 | B2 | | 5/2010 | Konno et al. |
| 2003/0035107 | A1 | * | 2/2003 | Overbeck .......... A61B 1/00052 356/405 |
| 2005/0171416 | A1 | * | 8/2005 | Proniewicz ........ A61B 5/14532 600/319 |
| 2006/0251408 | A1 | * | 11/2006 | Konno ................ A61B 5/4547 396/14 |
| 2007/0026363 | A1 | * | 2/2007 | Lehmann ........... A61C 13/0004 433/223 |

(Continued)

OTHER PUBLICATIONS

O. Mudanyali, et al., Integrated rapid-diagnostic-test reader platform on a cellphone, Lab Chip, 2012, 12(15), 2678-2686. (Year: 2012).*

(Continued)

*Primary Examiner* — Jeremiah C Hallenbeck-Huber

(57) ABSTRACT

Apparatuses and methods for producing improved photographs suitable for measuring teeth whiteness with a handheld camera using a camera jig are provided. The camera jig includes a base that contacts a surface. The camera jig also includes a light shield made from a tubular structure defining an interior cavity. The camera jig further includes a slot in the tubular structure that supports the handheld camera at a predetermined distance from a target, which may be teeth of a user. The slot aligns a lens of the handheld camera with the target. Further, the light shield blocks substantially all ambient light, other than light of a light source of the handheld camera, from the target as it is photographed.

12 Claims, 4 Drawing Sheets

(56) References Cited

U.S. PATENT DOCUMENTS

| | | | | |
|---|---|---|---|---|
| 2007/0141528 A1* | 6/2007 | Kobayashi | ............ | A61B 1/0008 433/29 |
| 2008/0024868 A1* | 1/2008 | Okamura | ................. | A61B 1/24 359/599 |
| 2009/0168063 A1* | 7/2009 | Kobayashi | ............. | A61C 19/10 356/404 |
| 2011/0211047 A1* | 9/2011 | Chhibber | ............. | A61B 5/0059 348/47 |
| 2013/0244197 A1 | 9/2013 | Tjioe | | |
| 2014/0182925 A1 | 7/2014 | Jang | | |
| 2015/0198522 A1* | 7/2015 | Wei | ...................... | G01N 21/251 356/421 |
| 2015/0213622 A1 | 7/2015 | Abdulwaheed | | |

OTHER PUBLICATIONS

Pohanka M. Photography by Cameras Integrated in Smartphones as a Tool for Analytical Chemistry Represented by an Butyrylcholinesterase Activity Assay. Star A, ed. Sensors (Basel, Switzerland). 2015;15(6): (Year: 2015).*

Kostelnik, Adam, Alexander Cegan, and Miroslav Pohanka. "Color Change of Phenol Red by Integrated Smart Phone Camera as a Tool for the Determination of Neurotoxic Compounds." Ed. Alexander Star. Sensors (Basel, Switzerland) 16.9 (2016): (Year: 2016).*

International Search Report and Written Opinion of related PCT/US2014/065592 dated Sep. 5, 2016.

* cited by examiner

COLOR MEASUREMENT JIG

BACKGROUND

Various at-home oral care systems for whitening teeth are available to consumers. These include whitening trays, pens, strips, mouth rinse, and toothpaste. Some products provide printed reference cards of different tooth shades to help consumers track their whitening progress. However, such cards are inconvenient because the consumer must make multiple comparisons in an attempt to find the one card that best matches the color of the consumer's teeth. Additionally, because such cards rely on the consumer's selection of a tooth and their judgment of a best match, the results are subjective. Further, because the consumer may attempt to use the cards under different lighting conditions, the results may vary over time due to changes in color and intensity of ambient lighting.

BRIEF SUMMARY

Embodiments of the present disclosure provide a jig for a handheld camera including a lens and a light source. The jig includes a base configured to be positioned over a surface. The jig also includes a light shield comprising a tubular structure defining an interior cavity. The jig further includes a slot in the light shield configured to support the handheld camera at a predetermined distance from the surface. The slot is proportioned to position the lens and the light source in the interior cavity and to align the lens of the handheld camera with at a target. The light shield blocks substantially all ambient light from the target.

Optionally, the base comprises an arch shape, the surface comprises buccal surfaces of teeth of the user, and the target comprises one or more of the teeth.

Optionally, the tubular structure comprises a first end abutting the base and a closed second end.

Optionally, wherein the slot in the light shield is substantially perpendicular to a central axis of the jig.

Optionally, the slot comprises: a first surface that directly contacts a lens-side surface of the handheld camera, a second surface that directly contacts a backside of the handheld camera, a distance from a bottommost surface of the base to the first surface corresponds to a minimum focusing distance of the handheld camera, and the slot receives the handheld camera in a snug manner that blocks substantially all ambient light from entering between the slot and the handheld camera.

Optionally, the jig further comprises a window in the base, and the slot aligns the lens with the target and the window.

Optionally, the tubular structure comprises a carton of an oral care product, and the slot comprises a removed section of the carton of the oral care product.

Embodiments of the present disclosure also provide a camera jig including a bottom surface including a window. The camera jig also includes a top surface. The camera jig further includes a tubular structure connecting the top surface and the bottom surface. The tubular structure defines an interior cavity between the top surface and the bottom surface. Additionally, the tubular structure includes a slot substantially perpendicular to a central axis of the camera jig. The slot aligns a lens of a handheld camera with the window and a target at a distance corresponding to a minimum focusing distance of the handheld camera. The camera jig blocks substantially all ambient light from reaching the target.

Optionally, the top surface is an entirely closed surface, the bottom surface comprises an arched shape, and the target comprises at least one tooth in a mouth of a user.

Optionally, the tubular structure comprises a carton of an oral hygiene product.

Embodiments of the present disclosure also provide a method of capturing teeth images using a handheld camera including a lens and a light source, and a camera jig including a base and a slot. The method includes positioning the base of the camera jig over buccal surfaces of teeth of a user. The method also includes inserting the handheld camera into the slot of the camera jig. Inserting the handheld camera in the slot of the camera jig includes placing the lens and the light source inside of the camera jig. Additionally, inserting the handheld camera in the slot includes aligning the lens with the teeth. Further, inserting the handheld camera in the slot includes blocking, by the camera jig, substantially all ambient light, other than light emitted from the light source, from the teeth. Moreover, the method includes capturing, using the handheld camera, an image of the teeth through the base of the camera jig.

Optionally, the method includes forming the base of the camera jig by removing a portion of a hollow product carton below a first predetermined location, such that the base is formed at the first predetermined location, and forming the slot of the camera jig by removing a partial section from the hollow product carton at a second predetermined location, the predetermined location being at distance equal to or greater than a minimum focusing distance of the handheld camera.

More optionally, the hollow product container is a carton for an oral care product.

Optionally, forming the slot of the camera jig comprises removing a partial section of the hollow product carton that is approximately equal to a thickness of the handheld camera and having a depth corresponding to a location of the lens of the handheld camera.

Embodiments of the present disclosure further provide a method comprising providing material capable of forming the jig of any one of the disclosed embodiments.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

Figure 1:
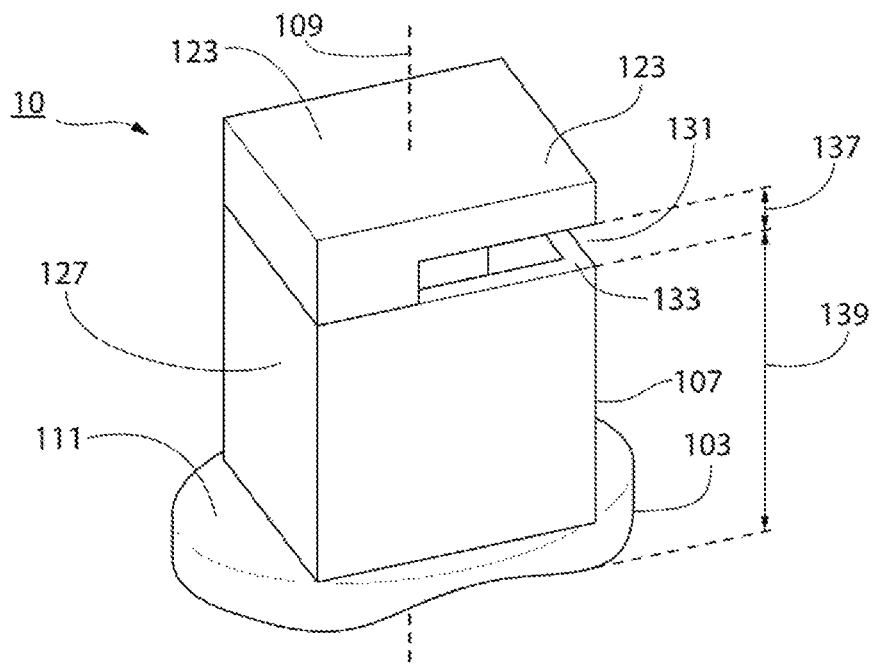
FIG. 1 illustrates a front perspective view of an exemplary camera jig in accordance with aspects of the present disclosure.
Figure 2:
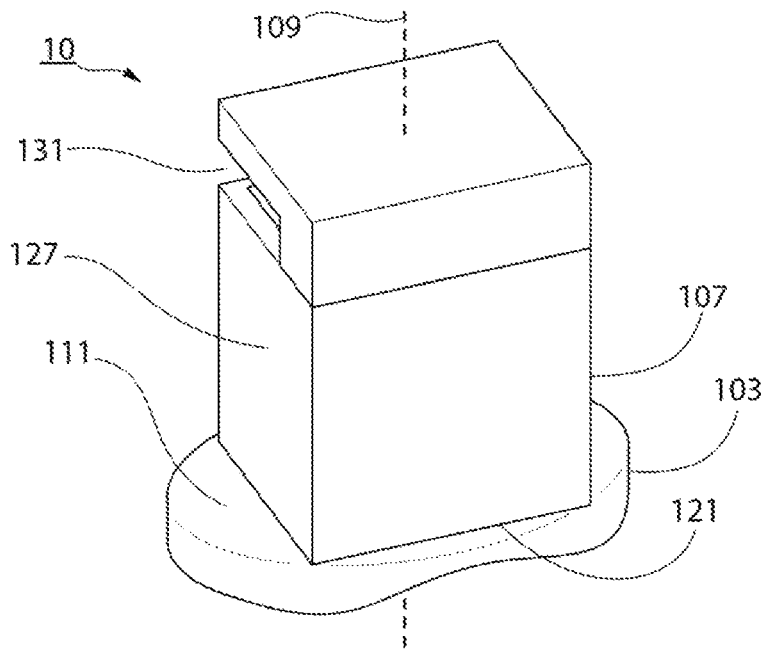
FIG. 2 illustrates a rear perspective view of an exemplary camera jig in accordance with aspects of the present disclosure.
Figure 3:
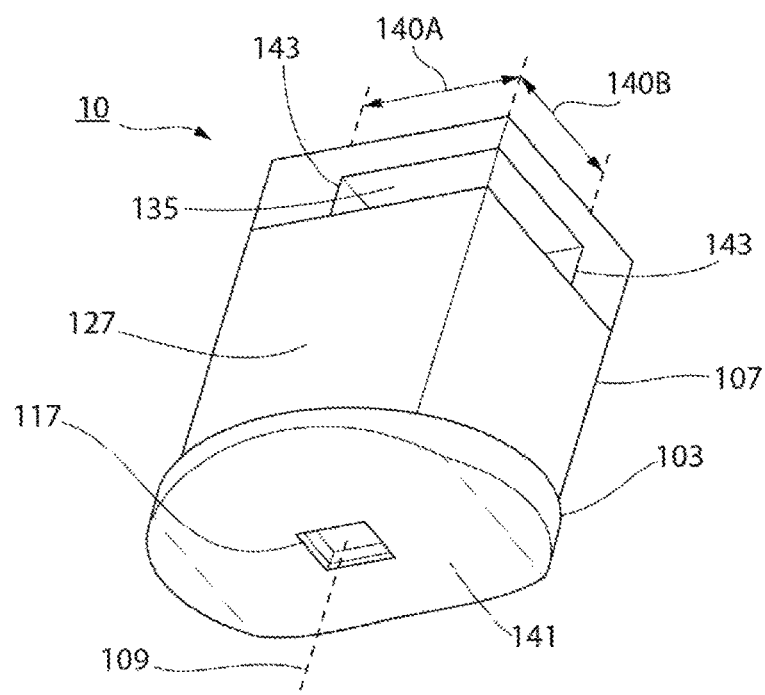
FIG. 3 illustrates a bottom perspective view of an exemplary camera jig in accordance with aspects of the present disclosure.

The present disclosure relates to measuring teeth whiteness and, more particularly, to a camera jig for measuring teeth whiteness with a handheld camera. Apparatuses and methods in accordance with aspects of the present disclosure provide a camera jig that prevents ambient lighting conditions from interfering with recording images (e.g., still pictures or video) of a user's (e.g., a consumer's) teeth with a camera. Rather, when images of the user's teeth are recorded using a handheld camera inserted in the disclosed camera jig, essentially the only light source that reaches the teeth and a lens of the camera is a built-in light source (e.g., a flash) of the camera. Additionally, in accordance with aspects of the present disclosure, the camera jig aligns the lens of the camera with the same target (i.e., one or more teeth) at the same distance throughout multiple uses. Thus, the camera jig disclosed herein enables users to capture images of a same target location under consistent light conditions, which allows for accurate evaluations of teeth whitening over time. In some embodiments, users can obtain (e.g., purchase or request) prefabricated camera jigs. For example, a provider of oral hygiene products can package the camera jig with an at-home teeth whitening product. However, in some embodiments disclosed herein, the design of the jig can be printed on a surface of an oral hygiene product carton (e.g., the box for a tube of whitening toothpaste) and the consumer can be provided instructions for modifying the carton (e.g., by punching out, cutting, folding and/or gluing) into a camera jig as described. In various embodiments, the camera may be part of a mobile phone.

FIGS. 1-4 respectively illustrate a first front perspective view, a rear perspective view, a bottom perspective view, and a second front perspective view of an exemplary camera jig 10 in accordance with aspects of the present disclosure. The camera jig 10 includes a base 103 and a light shield 107. In embodiments, the base 103 and the light shield 107 can be formed separately and combined to form the camera jig 10. In other embodiments, the base 103 and the light shield 107 can be manufactured as a single, unitary piece. For example, the base 103 and the light shield 107 can be printed together using a three-dimensional printer. Additionally, the base 103 and the light shield 107 can be formed together from a single product container (e.g., a toothpaste carton).

In accordance with aspects of the present disclosure, a user employs the camera jig 10 by positioning the base 103 on their mouth over buccal surfaces of the one or more teeth. In embodiments, the base 103 can have wings 111 that flare-out from the base 103 in a substantially perpendicular direction from a central axis 109 of the camera jig 10. In one employment technique, the user may place the base 103 inside their lips directly contacting buccal surfaces of teeth of a user. By holding the wings 111 in their mouth using the inside of their lips, a user can securely position the camera jig 10 in their mouth. In another employment technique, the user may place the base 103 against the outside of their opened, partially opened, or pursed lips, instead of directly against the buccal surfaces of their teeth. In embodiments the base 103 can have an arched shape corresponding to the arching of buccal surfaces of the user's mouth and/or teeth.

Further, in some embodiments, the base 103 can have soft and/or tacky coating (e.g., soft rubber or latex) to improve the grip and/or comfort for the user, as well as to better secure the camera jig 10 against the mouth of the user.

In embodiments, the base 103 includes a window 117 passing entirely through an uppermost and lowermost surface of the base 103. In accordance with aspects of the present disclosure, the window 117 is positioned such that it aligns with a lens 118 (see, e.g., FIG. 4) of the handheld camera 113 to provide a view of one or more target teeth when the camera jig 10 is held on a mouth of the user. For example, the camera jig 10 can align the lens 118 with the window 117 along the central axis 109 of the camera jig 10. In some embodiments, the perimeter (e.g., cross section) of the window 117 can be about the same size as a perimeter of the light shield 107. In some other embodiments, the perimeter of the window 117 can be substantially smaller than the circumference of the light shield 107. For example, the window 117 can have a perimeter of less than or equal to four (4) centimeters, whereas the perimeter of the light shield 107 can be greater than about sixteen (16) centimeters. By limiting the perimeter of the window 117, the camera jig 10 reduces the amount of light reflected by the user's gum and tongue back to the lens 118, which improves the accuracy and the consistency of images captured using the camera jig 10. Further, by making the perimeter of the window 117 small, the image of the tooth is limited to a correspondingly small target region, which increases accuracy of assessments by avoiding large variations in color that may occur across surfaces of the user's teeth. While the window 117 is illustrated as having a square shape, it is understood that it can have other shapes (e.g., circular, rectangular, triangular, ect.).

In accordance with aspects of the present disclosure, the light shield 107 is a tubular structure 127 having an open bottom end 121 physically connected to or integrated with the base 103, and a closed top surface 123 lacking any holes or other openings. In embodiments, a cross section of the tubular structure 127 has a substantially square shape. It understood, however, that the cross section of the tubular structure 127 can have other shapes (e.g., circular). The entirety of the bottom end 121 of the tubular wall 127 is connected to or integrated with the base 103 such that ambient light cannot enter the light shield 107 via the bottom end 121. And, because the base 103 is held in the mouth of the user or tight against the open portion of the lips when the camera jig 10 is in use, ambient light also cannot enter the light shield 107 via the window 117.

Figure 4:
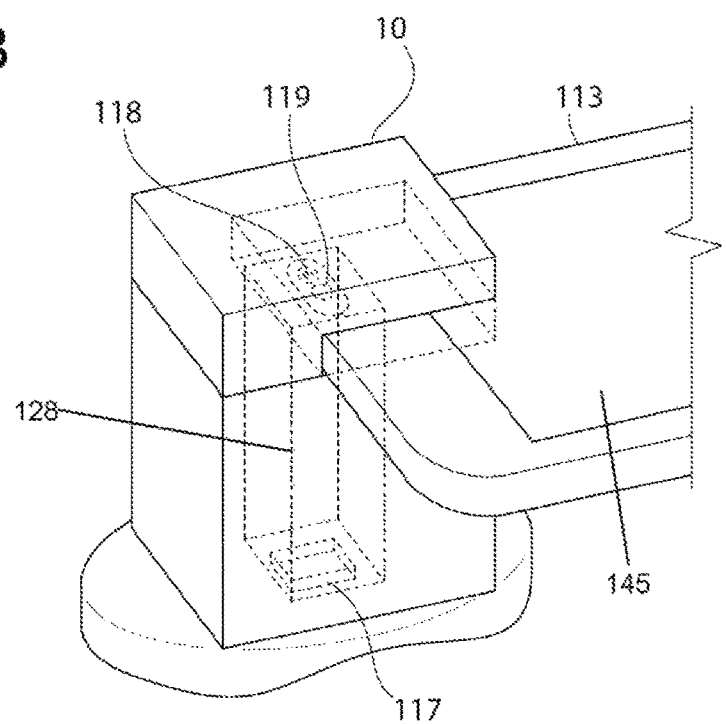
FIG. 4 illustrates a front perspective view of an exemplary camera jig and handheld camera in accordance with aspects of the present disclosure.

The tubular structure 127 is closed by the base 103 and the top surface 123, which all together define an interior cavity 128 that is entirely enclosed except for the window 117 and a slot 131. As illustrated in FIG. 4, the slot 131 can receive at least a portion of a handheld camera 113, including the lens 118 and a light source (e.g., a flash device) 119 of the handheld camera 113. In embodiments, the slot 131 comprises a first surface 133 that directly contacts a lens-side surface of the handheld camera 113, and a second surface 135 that directly contacts a backside of the handheld camera 113, and which is opposite of the first surface 133. In accordance with aspects of the present disclosure, a width 137 of the slot 131 between the first surface 133 and the second surface 135 is approximately equal to a thickness of the handheld camera 113 such that, when inserted into the slot 131, a reasonably snug fit is established between the camera jig 10 and the handheld camera 133. In some implementations, the slot 131 can be customized to fit with a particular model of a particular type of camera. For example, the handheld camera can be incorporated in a particular smartphone, such as an iPhone® 6 by Apple® Inc. of Cupertino Calif. In some exemplary implementations, the width 137 is greater than or equal to about 0.27 inches.

Additionally, in accordance with aspects of the present disclosure, the first surface 133 offsets the lens 118 of the camera a specific, predetermined distance 139 from a bottommost surface 141 of the base 103. In embodiments, the predetermined distance 139 is a distance at which the handheld camera 113 can focus clearly. For example, the distance 139 can be greater than or equal to a minimum focusing distance of the handheld camera 113. In some exemplary implementations, the distance 139 can be greater than or equal to about two (2.0) inches.

Further, in accordance with aspects of the current disclosure, the slot 131 may be substantially perpendicular to the central axis 109 and proportioned to align the lens 118 of the hndheld camera with the window 117. In embodiments, the window 117 is located in the middle of the base 103 along the central axis 109 of the camera jig 10. And, when the handheld camera 113 is fully inserted into the slot 131 such that a surface of handheld camera 113 directly contacts the bottom walls 133 of the slot 113, the lens 118 of the handheld camera 113 aligns with the window 117 along the central axis 109. For example, as shown in FIG. 4, slot 131 can be rectangular notch formed in directly adjacent sides of the rectangular tubular structure 127, wherein the shape and depths 140A, 140B of the rectangular notch correspond to a the shape of the handheld camera 113 (e.g., a smartphone). As such, when the handheld camera 113 is fully inserted in the slot 131 such that adjacent walls of the handheld camera 133 in direct contact with both innermost walls 143 of the slot 131, the lens 118 is securely positioned along the central axis 109 of the camera jig 10.

Moreover, in accordance with aspects of the present disclosure, the lens 118 and the flash 119 of the handled camera 113 are contained within the camera jig 10, while a viewfinder display 145 (e.g., a real-time LED display) remains substantially outside the camera jig 10. As such, in embodiments in which the lens 118 is on a same side of the handheld camera 113 as the viewfinder display 145, a user can view their teeth using the viewfinder display 145 while capturing an image.

While FIG. 4 shows an exemplary handheld camera 113 having a lens 118 and light source 119 positioned toward an upper corner, it is understood that other camera devices may position the lens and/or light source in different locations, such as along a centerline of the camera device. Nevertheless, it will be recognized that the camera jig 10 and/or light source 119 can be located in other positions. Accordingly, the slot 131 can be proportioned to align such cameras with the centerline 109 and/or the window 117. For example, the innermost walls 143 can be proportioned such that a lens of a phone having lens positioned on a centerline will align the window 117.

Figure 5:
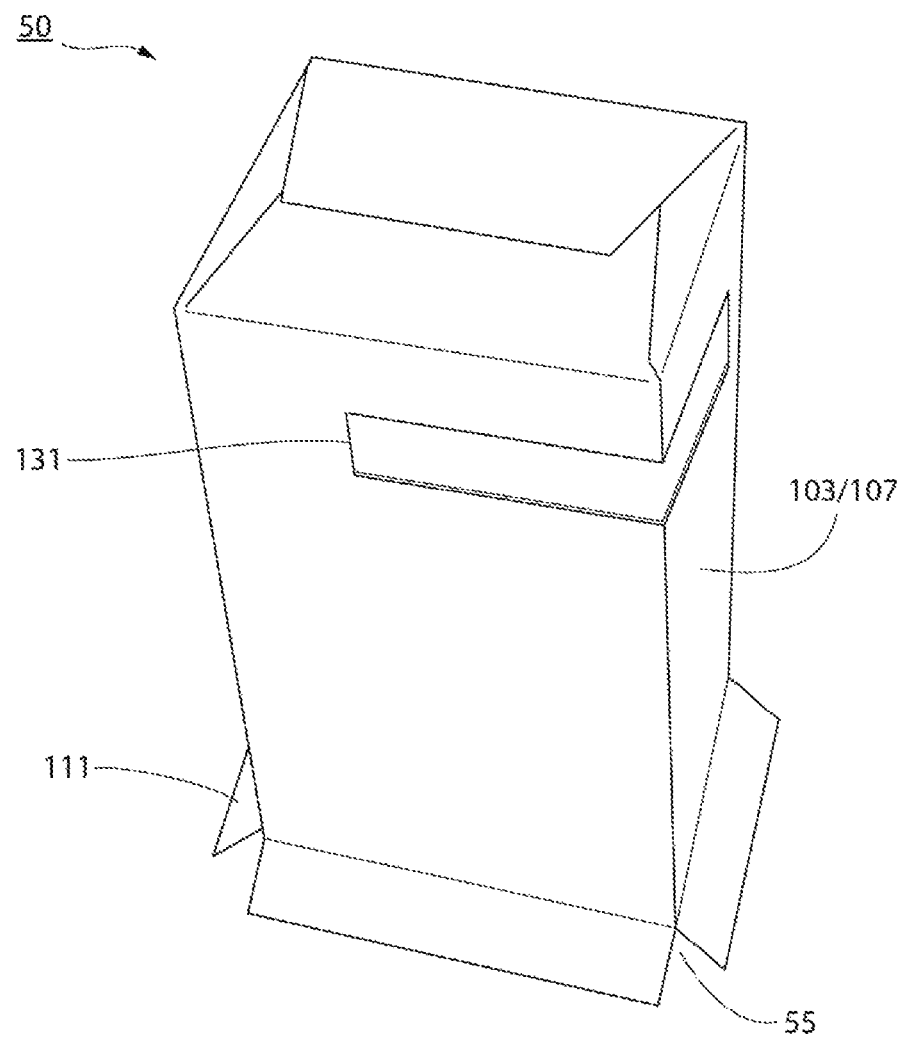
FIG. 5 illustrates a front perspective view of an exemplary camera jig in accordance with aspects of the present disclosure.

FIG. 5 illustrates a front perspective view of an exemplary camera jig 50 in accordance with aspects of the present disclosure. The camera jig 50 may be substantially the same or similar to that previously described herein (e.g., camera jig 10). In accordance with aspects of the present disclosure, the camera jig 50 can be constructed from a hollow product container. For example, the camera jig 50 can be formed from a carton for a tube of oral care product (e.g., toothpaste or the like). In such embodiments, the base 103 and the light shield 107 of the camera jig 50 can be a single unit (i.e., 103/107) formed by removing (e.g., cutting-off or breaking-off at perforations) a portion (e.g., 33% or 50%) of the hollow product carton below a first predetermined location. Also, in some implementations, the camera jig 50 can include splits or perforations at the bottommost corners 55 of the product container, which may be separated and folded to form wings 111 in the base 103. Additionally, the slot 131 can be formed by removing a partial section from the hollow product carton at a second predetermined distance (e.g., distance 139) from the base corresponding to at least the minimum focusing distance of the handheld camera, or longer. And, as previously described, the section forming the slot 131 can have a width (e.g., width 137) and depths 140A, 140b corresponding to a specific make and model of handheld camera such that a lens and light source of the handheld camera substantially align with a central axis (e.g., central axis) 109 of the camera jig 50 and such that the handheld camera fits snugly into the slot 131 with substantially no light leaks.

As described previously herein, the product container can be fabricated with markings and/or perforations indicating the locations that require cutting to form the camera jig 50. In some embodiments, the section of the hollow product container that must be removed to form the slot 131 may be perforated around the edges, such that user can punch out that section of the container without using tools. Similarly, there may be perforations to aid in removing the portion of the original product container that was below the wings 111. Additionally, some or all of the material forming the product container can have a substantially waterproof surface (e.g., wax) or can be formed from a substantially waterproof material (e.g., plastic), that avoids damage due to moisture in a mouth of a user.

Figure 6:
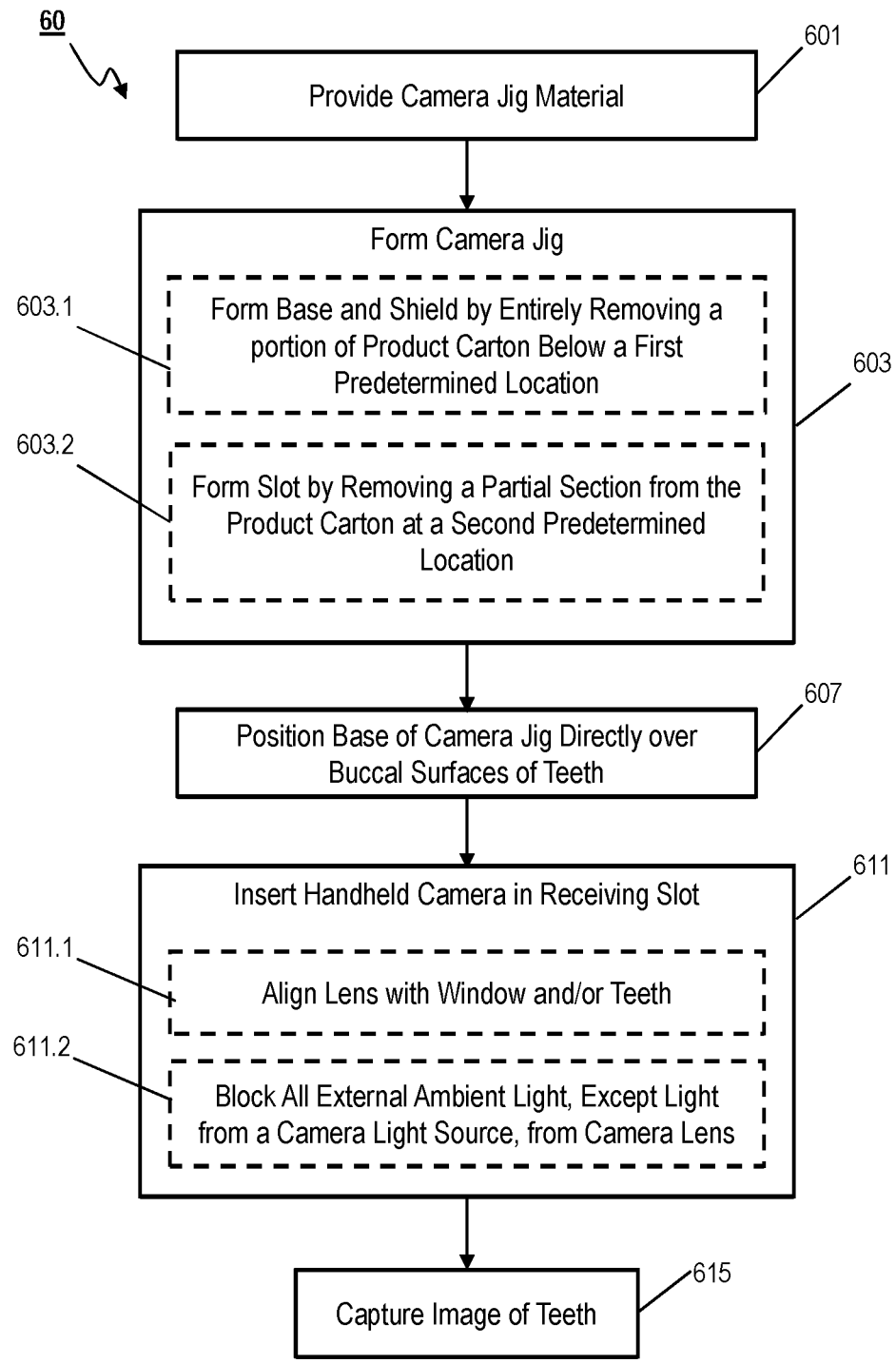
FIG. 6 illustrates a flow diagram of an exemplary process for using a camera jig in accordance with aspects of the present disclosure.

FIG. 6 illustrates a flow diagram of an exemplary process 60 for forming and using a camera jig (e.g., camera jig 10 or camera jig 50) in accordance with aspects of the present disclosure. At 601, a user can be provided material for forming the camera jig. As described previously herein, the material can be a product container, such as an oral care hygiene product carton. In embodiments, the material can include markings, perforations and/or instructions for forming the camera jig, as described previously herein. At 603 the user can form the camera jig (e.g., camera jig 50) as previously described herein. In embodiments, as indicated at 603.1, forming the camera jig can include forming a base (e.g., base 103) and light shield (e.g., light shield 107) by removing a portion of the product carton below a first predetermined location, as previously described herein. Further, as indicated at 603.2, forming the camera jig can include forming a slot (e.g., slot 131) by removing a partial section from the product carton, as previously described herein. In accordance with aspects of the present disclosure, the partial section is removed at a second predetermined distance (e.g., distance 139, which may be e.g., equal to or greater than the minimum focusing distance of a handheld camera) and depths (e.g., depths 140A, 140B) corresponding to a location of a lens location of particular handheld camera such that its lens substantially aligns with a central axis. At 607, the user positions the base of the camera jig directly over the buccal surfaces of their teeth in a manner that blocks out external light. For example, the user can press the base of the camera jig onto their teeth and hold the base (e.g., via wings 111) security in position using the inside of their lips, or the user can press the jig onto outside of their open lips.

At 611, the user inserts a handheld camera (e.g., handheld camera 113) into the slot of the camera jig. As indicated at 611.1, fully inserting the handheld camera into the slot aligns the lens of the handheld camera with a window (e.g., window 117) or an open end in the base of the camera jig and/or with one or more particular teeth of the user. Additionally, as indicated at 611.2, fully inserting the handheld camera into the slot blocks all external ambient light from the interior of the camera jig. At 615, the user captures an image (e.g., a flash-lit digital photograph) of one or more teeth using the handheld camera inside the camera jig. As discussed previously, in situations where the lens is on a same side of the camera as the viewfinder (e.g., viewfinder display 145), the user can view the display while capturing an image of their teeth.

As detailed above, camera jigs in accordance with aspects of the present disclosure enable a user to consistently align the camera with the same one or more teeth and take multiple pictures under the same lighting and distance conditions as the user tracks their whitening progress over time (e.g. days, weeks or longer). Because the target of the camera and the picture-taking conditions are essentially the same for every image captured, users can make reliable comparisons. As noted previously, the camera jig isolates the lens of the camera from ambient light such the only light source for the images captured using the camera jig is that of the camera (e.g., the camera's flash). Because the color and illumination level produced by the light source is the same for each image captured over time, the image's capturing of the color of the teeth does not vary because of variations in the teeth's illumination, and a comparison of the tooth color across the images captured can be more accurate. Accordingly, the camera jig disclosed herein allows the user to make accurate comparisons of the images captured over time to track the progress of a teeth-whitening regimen. Further, the consistency of the images provided by the disclose camera jig enables accurate computer-based comparisons of the images captured over time.

It is understood that the functions and/or operations illustrated in a particular block of the FIG. 6 can occur out of the order shown. For example, blocks 603.1 and 603.2 shown in succession can be executed substantially concurrently, or blocks 603.1 and 603.2 can be executed in the reverse order). For another example, the camera 113 may be placed into the slot 131 of the camera jig before the camera jig is positioned on or over the teeth.

The forgoing description of the preferred embodiment(s) is merely exemplary in nature and is in no way intended to limit the invention, its application, or uses. The above features have been described in detail with particular reference to certain preferred embodiments thereof, but it will be understood that variations and modifications can be effected within the spirit and scope of the disclosure. One of skill in the art will appreciate that each of the above are exemplary implementations and are not to be construed as a limitation on the scope of the present disclosure.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in any ensuing claims are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A jig for a handheld camera comprising a lens and a light source, the jig comprising:
   a base configured to be positioned over a surface;
   a light shield comprising a tubular structure defining an interior cavity, the tubular structure comprises a toothpaste carton, and
   a slot in the light shield configured to removably receive and support the handheld camera at a predetermined distance from the surface, the slot formed as an opening extending into the jig from an outer wall thereof by a predetermined depth,
   wherein:
     the slot is proportioned to position the lens and the light source in the interior cavity and to align the lens of the handheld camera with a target,
     the slot comprises a removed section of the toothpaste carton, and
     the light shield blocks substantially all ambient light from the target.

2. The jig of claim 1, wherein:
   the base comprises an arch shape;
   the surface comprises buccal surfaces of teeth of the user; and
   the target comprises one or more of the teeth.

3. The jig of claim 1, wherein the tubular structure comprises a first end abutting the base and a closed second end.

4. The jig of claim 1, wherein the slot in the light shield is substantially perpendicular to a central axis of the jig.

5. The jig of claim 1, wherein:
   the slot comprises:
     a first surface that directly contacts a lens-side surface of the handheld camera; and
     a second surface that directly contacts a backside of the handheld camera,
   a distance from a bottommost surface of the base to the first surface corresponds to a minimum focusing distance of the handheld camera, and
   the slot receives the handheld camera in a snug manner that blocks substantially all ambient light from entering between the slot and the handheld camera.

6. The jig of claim 1, further comprising:
   a window in the base,
   wherein the slot aligns the lens with the target and the window.

7. A camera jig comprising:
   a bottom surface including a window;
   a top surface; and
   a tubular structure connecting the top surface and the bottom surface, the tubular structure defining an interior cavity between the top surface and the bottom surface, wherein:
the tubular structure comprises a slot substantially perpendicular to a central axis of the camera jig, the slot formed as an opening extending into the jig from an outer wall thereof by a predetermined depth;
the slot aligns a lens of a handheld camera with the window and a target at a distance corresponding to a minimum focusing distance of the handheld camera; and
the camera jig blocks substantially all ambient light from reaching the target.

8. The camera jig of claim 7, wherein:
the top surface is an entirely closed surface;
the bottom surface comprises an arched shape; and
the target comprises at least one tooth in a mouth of a user.

9. The camera jig of claim 7, wherein the tubular structure comprises a toothpaste carton.

10. A method comprising:
forming the base of a camera jig by removing a portion of a toothpaste carton below a first predetermined location, such that the base is formed at the first predetermined location, the camera jig including a base and a slot;
forming the slot of the camera jig by removing a partial section from the toothpaste carton at a second predetermined location, the predetermined location being at a distance equal to or greater than a minimum focusing distance of the handheld camera;
positioning the base of the camera jig over buccal surfaces of one or more teeth of a user;
after positioning the base of the camera jig over the buccal surfaces, inserting a handheld camera into the slot of the camera jig, the handheld camera including a lens and a light source, wherein inserting the handheld camera in the slot of the camera jig comprises:
placing the lens and the light source inside of the camera jig;
aligning the lens with the one or more teeth; and
blocking, by the camera jig, substantially all ambient light, other than light emitted from the light source, from the one or more teeth; and
capturing, using the handheld camera, an image of the one or more teeth through the base of the camera jig.

11. The method of claim 10, wherein forming the slot of the camera jig comprises removing a partial section of the toothpaste carton that is approximately equal to a thickness of the handheld camera and having a depth corresponding to a location of the lens of the handheld camera.

12. The method of claim 10, further comprising viewing the image on a viewfinder display, the viewfinder display located substantially outside the camera jig.

* * * * *